(12) United States Patent
Conn et al.

(10) Patent No.: US 7,531,541 B2
(45) Date of Patent: May 12, 2009

(54) PARTIAL MGLUR5 ANTAGONISTS FOR TREATMENT OF ANXIETY AND CNS DISORDERS

(75) Inventors: P. Jeffrey Conn, Brentwood, TN (US); Alice L. Rodriguez, Nashville, TN (US); Carrie K. Jones, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 11/523,873

(22) Filed: Sep. 20, 2006

(65) Prior Publication Data

US 2007/0208028 A1    Sep. 6, 2007

Related U.S. Application Data

(60) Provisional application No. 60/718,298, filed on Sep. 20, 2005, provisional application No. 60/742,516, filed on Dec. 6, 2005.

(51) Int. Cl.
*A61K 31/497* (2006.01)
*C07D 239/42* (2006.01)

(52) U.S. Cl. .................................. 514/252.1; 514/256
(58) Field of Classification Search ............... 514/252.1, 514/256
See application file for complete search history.

(56) References Cited

U.S. PATENT DOCUMENTS 6,890,931 B2 * 5/2005 Bear et al. ................... 514/277
6,956,049 B1 * 10/2005 Cosford et al. .............. 514/365
7,205,411 B2    4/2007 Bolea et al.
2001/0056084 A1  12/2001 Allgeier et al.

OTHER PUBLICATIONS

Alagille et al., "Functionalization at position 3 of the phenyl ring of the potent mGluR5 noncompetitive antagonists MPEP," *Bioorg Med Chem Lett* 15:945-949 (2005).
Alagille et al., "Synthesis and receptor assay of aromatic-ethynl-aromatic derivatives with potent mGluR5 antagonist activity," *Bioorg Med Chem* 13(1):197-209 (2005).
Arunlakshana et al., "Some quantitative uses of drug antagonist," Br J Phalinacol 120(4 Suppl):151-161 (1958).
Awad et al., "Activation of metabotropic glutamate receptor 5 has direct excitatory effects and potentiates NMDA receptor currents in neurons of the subthalamic nucleus," *J. Neurosci* 20:7871-7879 (2000).
Cosford et al., "[3H]-methoxymethyl- MTEP and [3H]-methoxy-PEPy: potent and selective radioligands for the metabotropic glutamate subtype 5 (mGluR5) receptor," *Bioorg Med Chem Lett* 13(3):351-354 (2003).
Erratum in: *Curr Drug Target CNS Neurol Disord* (4):449 (2002).
Gasparini et al., "Allosteric modulators of group I metabotropic glutamate receptors: novel subtype-selective ligands and therapeutic perspectives," *Cun Opin Pharmacol* 2:43-9 (2002).

Kenny et al., "The ups and downs of addiction: role of metabotropic glutamate receptors," *Trends Pharmacol Sci* 25(5):265-72. Review (2004).
Kinney et al., "A novel selective positive allosteric modulator of metabotropic glutamate receptor subtype 5 has in vivo activity and antipsychotic-like effects in rat behavioral models," *J. Pharmacol Exp Ther* 313:199-206 (2005).
Lindsley et al., "Discovery of positive allosteric modulators for the metabotropic glutamate receptor subtype 5 from a series of N-(1,3-diphenyl-IH- pyrazol-5yl)benzamides that potentiate receptor function in vivo," *J Med Chem* 47:5825-5828 (2004).
Marino et al., "Activation of group I metabotropic glutamate receptors produces a direct excitation and disinhibition of GABAergic projection neurons in the substantia nigra pars reticulate," *J Neurosci* 21:7001-7012 (2001).
Marino et al., "Modulation of the basal ganglia by metabotropic glutamate receptors: potential for novel therapeutics," *Curr Drug Targets CNS Neurol Disord* 1(3):239-250 (2002).
Marino et al., "Direct and indirect modulation of the N-methyl D-aspartate receptor," *Cun Drug Targets CNS Neurol Disord* 1(1):1-16 (2002).
Moghaddam "Targeting metabotropic glutamate receptors for treatment of the cognitive symptoms of schizophrenia," *Psychopharmacology* (Berl). 174(1):39-44 Epub (2004).

(Continued)

*Primary Examiner*—Raymond J Henley, III
(74) *Attorney, Agent, or Firm*—Ballard Spahr Andrews & Ingersoll, LLP

(57) ABSTRACT

Provided is a method of treating conditions and disorders for which full mGluR5 antagonists are potentially effective, such as, e.g., anxiety, epilepsy, schizophrenia and other psychotic disorders, Parkinson's disease, addictive disorders, and the like in a subject in need of such treatment, comprising administration to such subject of a therapeutically effective amount of a partial, non-competitive mGluR5 antagonist compound of the invention. Specific examples of partial MgluR5 antagonists provided include those compounds having the formula:

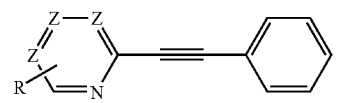

wherein:
Z is, independently N or —CH—, provided that one, and only one Z is N;
R is halogen (e.g., Br, F and the like), alkyl (e.g., methyl), alkenyl (e.g., CH=CH2, aryl (e.g., phenyl), heterocyclic (e.g., thiophenyl).

22 Claims, 10 Drawing Sheets

OTHER PUBLICATIONS

NARSAD grant "Allosteric Potentiators of mGluR5 as a Novel Approach for Treatment of Schizophrenia," Date not provided.

NIH grant F32 NS049865 Date not provided.

NIH/NIMH R01 MH062646 - "Regulation of Signaling by mGluR5," Date not provided.

O'Brien et al., "A family of highly selective allosteric modulators of the metabotropic glutamate receptor subtype 5," *Mol Pharmacol* 64:731-740 (2003).

O'Brien et al., " A Novel Selective Allosteric Modulator Potentiates the Activity of Native Metabotropic Glutamate Receptor Subtype 5 in Rat Forebrain," *J Pharmacol Exp Ther* 309:568-577 (2004).

Rodriguez et al., "A close structural analog of 2-methyl-6-(phenylethynyl)-pyridine acts as a neutral allosteric site ligand on metabotropic glutamate receptor subtype 5 and blocks the effects of multiple allosteric modulators," *Mol Pharmacol* 68(6):1793-1802 (2005).

Spooren et al., "mGluR5 receptor antagonists: a novel class of anxiolytics?" *Drug News Perspect* 17(4):251-7 (2004).

Spooren et al., "Novel allosteric antagonists shed light on mglu(5) receptors and CNS disorders," *Trends Pharmacol Sci* 22(7):331-337 (2001).

Swanson et al., "Metabotropic glutamate receptors as novel targets for anxiety and stress disorders," *Nat Rev Drug Discov* 4(2):131-144 (2005).

Varney et al. "Metabotropic glutamate receptor involvement in models of acute and persistent pain: prospects for the development of novel analgesics," *Curr Drug Targets CNS Neurol Disord* 1(3):283-296 (2002).

\* cited by examiner

PARTIAL MGLUR5 ANTAGONISTS FOR TREATMENT OF ANXIETY AND CNS DISORDERS

CROSS-REFERENCE TO RELATED APPLICATIONS

This application claims the benefit of U.S. provisional application No. 60/718,298 filed on Sep. 20, 2005 and U.S. provisional application No. 60/742,516 filed on Dec. 6, 2005. The aforementioned applications are herein incorporated by this reference in its entirety.

ACKNOWLEDGEMENT OF GOVERNMENT SUPPORT

This work was supported by NARSAD grant "Allosteric Potentiators of mGluR5 as a Novel Approach for Treatment of Schizophrenia," NIH/NIMH R01 MH062646-"Regulation of Signaling by mGluR5," and NIH grant F32 NS049865. The government has certain rights in the invention.

FIELD OF THE INVENTION

The present invention relates to new compounds and their pharmaceutical uses based on their having partial, non-competitive antagonistic activity at the metabotropic glutamate receptors (mGluR5).

BACKGROUND OF THE INVENTION

Glutamate is the major excitatory neurotransmitter in the central nervous system, exerting its effects through both ionotropic and metabotropic glutamate receptors (mGlu receptors). The mGlu receptors are members of the family C G protein-coupled receptors (GPCRs), distinguished from other families of GPCRs by a large extracellular N-terminal agonist binding site (see Conn P J and Pin J P (1997) Pharmacology and functions of metabotropic glutamate receptors, Annu Rev Pharmacol Toxicol 37:205-37 and Pin J P and Acher F (2002). The metabotropic glutamate receptors: structure, activation mechanism and pharmacology, Curr Drug Targets CNS Neurol Disord 1:297-317 for reviews). The mGlu receptors provide a mechanism by which glutamate can modulate or fine tune activity at the same synapses at which it elicits fast synaptic responses. There are eight known members of the mGlu family, divided into three groups based on sequence homology, pharmacology and coupling to intracellular signaling pathways. Group I mGlu receptors (mGlu I and mGluR5) are primarily localized at postsynaptic sites and couple to Gαq and increases in intracellular calcium. Group II (mGlu2 and mGlu3) and group III (mGlu4, mGlu6, mGlu7 and mGlu8) mGlu receptors are predominantly localized presynaptically, and couple to Gαi/o and associated effectors such as inhibition of adenylyl cyclase and various ion channels.

The group I receptor mGluR5 has been implicated in a number normal physiological processes in the central nervous system (CNS) and previous studies suggest that selective agonists and antagonists of mGluR5 could have utility for treatment of a number of CNS disorders, including pain (Varney M A and Gereau R W (2002) Metabotropic glutamate receptor involvement in models of acute and persistent pain: prospects for the development of novel analgesics. Curr Drug Target CNS Neurol Disord 1:283-96), anxiety disorders (Swanson C J, Bures M, Johnson M P, Linden A M, Monn J A and Schoepp D D (2005) Metabotropic glutamate receptors as novel targets for anxiety and stress disorders. Nat Rev Drug Discov 4: 131-44. Spooren W and Gasparini F (2004) mGluR5 receptor antagonists: a novel class of anxiolytics? Drug News Perspect 17:251-7), Parkinson's disease (Marino M J and Conn J P (2002) Modulation of the basal ganglia by metabotropic glutamate receptors: potential for novel therapeutics. Curr Drug Target CNS Neurol Disord 1:23950), addiction (Kenny P J and Markou A (2004) The ups and downs of addiction: role of metabotropic glutamate receptors. Trends Pharmacol Sci 25:265-72) and schizophrenia (Marino M J, Wittmann M, Bradley S R, Hubert G W, Smith Y and Conn P J (2001) Activation of group I metabotropic glutamate receptors produces a direct excitation and disinhibition of GABAergic projection neurons in the substantia nigra pars reticulata. J Neurosci 21:7001-12; Moghaddam B (2004) Targeting metabotropic glutamate receptors for treatment of the cognitive symptoms of schizophrenia. Psychopharmacology (Berl) 174:39-44).

Unfortunately, it has been difficult to develop compounds that act as selective ligands at the orthosteric glutamate binding site of mGluR5 or other individual mGlu subtypes that have properties that are likely to be suitable for development of therapeutic agents.

It is an object of the invention to provide novel partial mGluR5 antagonist compounds that do not suffer from disadvantageous side-effects, but which still offer therapeutic activity.

SUMMARY OF THE INVENTION

The above and other objects are realized by the present invention, one embodiment of which relates to partial, non-competitive mGluR5 antagonist compounds, excluding 2-(2-(3-methoxyphenyl)ethynyl)-5-methyl pyridine (M-5MPEP) and 2-(2-(5-bromopyridin-3-yl)ethynyl)-5-methylpyridine (Br-5MPEPy), effective for the treatment of conditions and disorders for which full mGluR5 antagonists may be effective, such as, e.g., anxiety, epilepsy, schizophrenia and other psychotic disorders, Parkinson's disease, addictive disorders, and the like.

In a further embodiment the partial non-competitive mGluR5 antagonist compounds exclude N-(1,3-diphenyl-IH-pyrazol-5yl)benzamides; N-[4-chloro-2-[(1,3-dioxo-1,3-dihydro-2H-isoindol-2-yl)methyl]phenyl]-2hydroxybenzamide (CPPHA); 3,3'-difluorobenzaldazine (DFB); 2-methyl-6-(phenylethynyl)-pyridine (MPEP); and 3-[(2-methyl-1,3-thiazol-4-yl)ethynyl]pyridine (MTEP).

Specific examples of partial MgluR5 antagonists of the invention include those compounds having the formula:

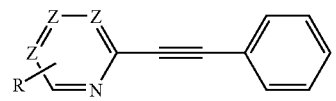

wherein:
Z is, independently N or —CH—, provided that one, and only one Z is N;
R is halogen (e.g., Br, F and the like), alkyl (e.g., methyl), alkenyl (e.g., CH=CH2, aryl (e.g., phenyl), heterocyclic (e.g., thiophenyl).

A further embodiment of the invention provides the use of the above partial, non-competitive mGluR5 antagonist compounds of the invention for the treatment of conditions and disorders for which full mGluR5 antagonists are potentially effective, such as, e.g., anxiety, epilepsy, schizophrenia and other psychotic disorders, Parkinson's disease, addictive disorders, and the like.

A still further embodiment of the invention concerns the use of the partial, non-competitive mGluR5 antagonist compounds of the invention in the manufacture of a pharmaceutical composition for the treatment of any of the above-described conditions and disorders.

An additional embodiment of the invention provides a method of treating any of the above-described conditions and disorders in a subject in need of such treatment, comprising administration to such subject of a therapeutically effective amount of a partial, non-competitive mGluR5 antagonist compound of the invention.

In a further embodiment of the methods and uses related to treating the disorders disclosed herein, examples of partial MgluR5 antagonists of the invention include compounds having the formula:

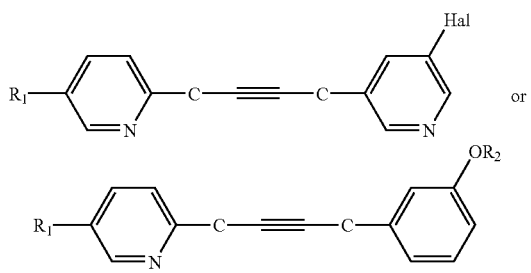

wherein $R_1$ is a halogen (e.g., F), alkyl group (e.g., methyl), alkenyl group (e.g., CH=Ch$_2$, aryl group (e.g., phenyl), heterocyclic group (e.g., thiophenyl), and the like.

$R_2$ is an alkyl group and Hal is a halogen.

Another embodiment of the invention relates to a pharmaceutical composition incorporating as active agent an effective amount of a partial, non-competitive mGluR5 antagonist compound of the invention for use in the treatment of any of the above-described conditions and disorders.

A further embodiment of the invention concerns an article of manufacture comprising packaging material and a pharmaceutical agent contained within the packaging material, wherein the pharmaceutical agent is effective for the treatment of a subject suffering from any of the above-described conditions and disorders, and wherein the packaging material comprises a label which indicates that the pharmaceutical agent can be used for ameliorating the symptoms associated with the condition or disorder, and wherein the pharmaceutical agent is a partial, non-competitive mGluR5 antagonist compound, excluding 2-(2-(3-methoxyphenyl)ethynyl)-5-methyl pyridine (M-5MPEP) and 2-(2-(5-bromopyridin-3-yl)ethynyl)-5-methylpyridine (Br-5MPEPy), effective therefor.

DETAILED DESCRIPTION OF THE INVENTION

Figure 1:
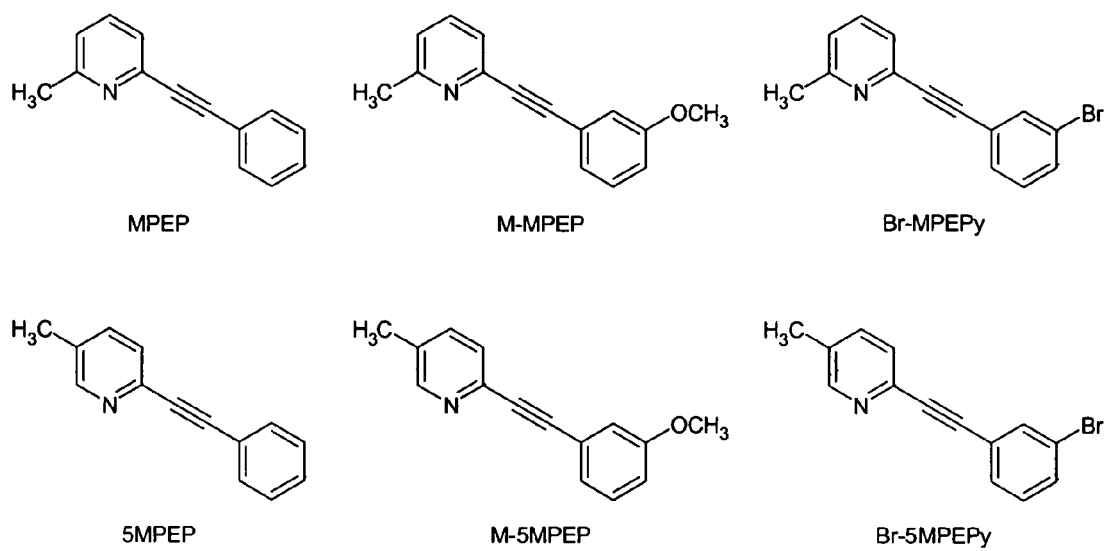
FIG. 1. Chemical structures of allosteric ligands of mGluR5.

The present invention is predicated on the discovery that compounds that function as partial mGluR5 antagonists, excluding 2-(2-(3-methoxyphenyl)ethynyl)-5-methyl pyridine (M-5MPEP) and 2-(2-(5-bromopyridin-3-yl)ethynyl)-5-methylpyridine (Br-5MPEPy), that bind to the MPEP site on mGluR5 but have only partial inhibition effects on the mGluR5 response are useful for the treatment of the same conditions and disorders for which full mGluR5 antagonists are useful, but do not suffer from the same disadvantages associated with the latter. Exemplary of these compounds are compounds provided below which act as "partial antagonists" of mGluR5 in that they only partially inhibit the response of this receptor to glutamate. These are clearly distinct from partial agonists at orthosteric sites in that they do not activate the receptor.

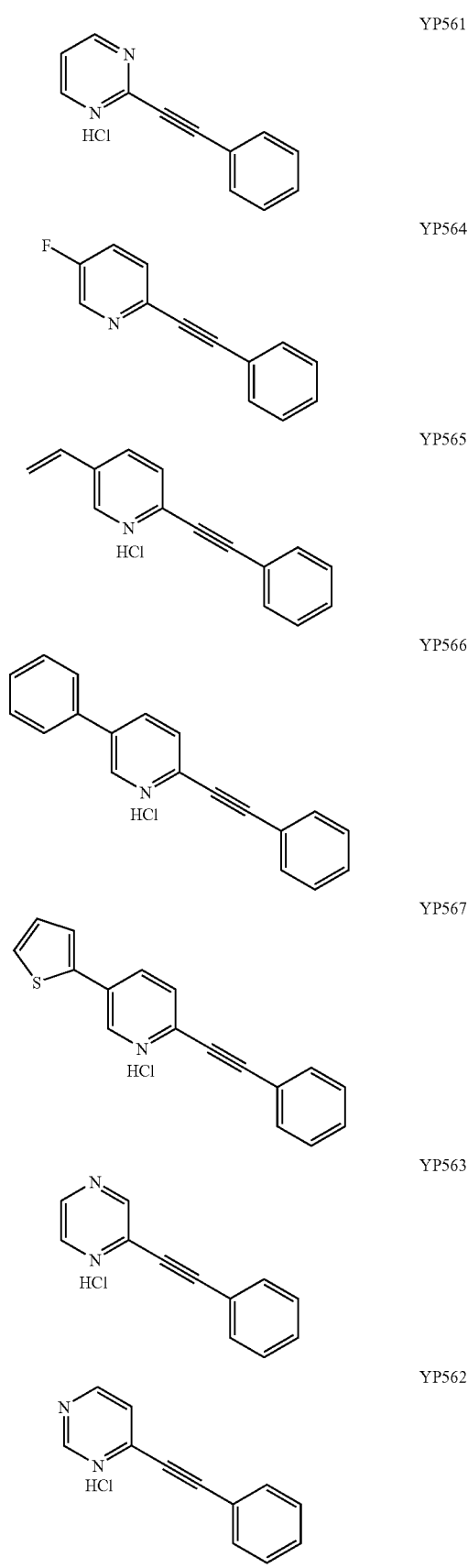

-continued

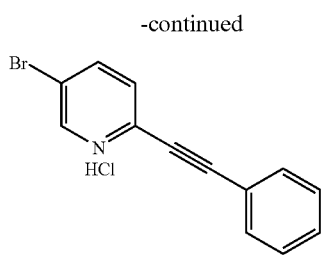

YP260

It will be appreciated by those skilled in the art that the above-described specific compounds and classes of compounds are merely exemplary of the compounds of the invention and that the invention includes any compound which is a partial mGluR5 antagonist.

"A partial mGluR5 antagonist" of the invention can be an antagonist that exhibits a statistically significant antagonist activity that is statistically significantly less than the antagonist activity, for example, of MPEP.

The "partial mGluR5 antagonists" of the invention are useful for the treatment of anxiety and other related nervous system disorders, such as those mentioned above which provide the benefits of mGluR5 antagonists without the adverse side-effects and/or the development of tolerance.

Anxiety is a fear, apprehension, or dread of impeding danger often accompanied by restlessness, tension, tachycardia, and dyspnea. Other symptoms commonly associated with anxiety include depression, dysthymic disorder, panic disorder, agoraphobia, and other specific phobias, eating disorders, and many personality disorders. In many clinical cases, anxiety is not associated with a clearly defined and treatable primary illness. While in other cases in which a treatable primary disorder is identified, it can be desirable to treat anxiety at the same time as the primary illness. Benzodiazepines are the most commonly prescribed anti-anxiety drugs for the treatment of generalized anxiety disorder and severe anxiety accompanied with panic attacks. However, benzodiazepines produce dose-limiting side effects, including impairment of motor functions and normal cognition, particularly in the elderly, that often result in confusion, delirium and falls with fractures. Sedatives are also commonly used for the treatment of generalized anxiety disorders; while azapirones, such as buspirone, are often prescribed for the treatment of moderate anxiety conditions. Sedatives and azapirones are also associated with dose-limiting impairments in motor function and cognition (Tatarczynska et al., (2001) Br. J. Pharmacol. 132(7):1423-1430; Will et al., (2001) Trends in Pharmacological Sciences 22(7):331-337).

Thus, there is a need for novel methods for the treatment of generalized anxiety disorder and other nervous system disorders that provide efficacy within a dose range that does not produce corresponding motor and/or cognitive side effects.

Within the mammalian central nervous system, glutamate is the primary excitatory neurotransmitter and is responsible for the generation of fast excitatory synaptic responses at most CNS synapses. Ionotropic glutamate receptors (iGluRs), including the N-methyl-D-aspartate (NMDA) receptor subtype, are a well characterized family of glutamate receptor cation channels that are responsible for mediating fast synaptic responses at glutamatergic synapses. In addition, glutamate activates metabotropic glutamate receptors (mGluRs), which are coupled to effector systems, through GTP-binding proteins. Group I mGluRs, include mGluR1 and mGluR5, which couple primarily to increases in phosphoinositide hydrolysis in expression systems whereas group II (mGluRs 2 and 3) and group III (mGluRs 4, 6, 7, and 8) mGluRs couple primarily to inhibition of adenylyl cyclase when expressed in cell lines. Modulation of mGluR subtypes provides a mechanism by which glutamate can modulate or fine tune activity at the same synapses at which it elicits fast synaptic responses. In particular, the modulation of group I receptor mGluR5 has been implicated in a number of pathological CNS conditions including chronic pain, anxiety, Parkinson's disease, addiction and schizophrenia.

Previous studies have demonstrated that two selective and non-competitive antagonists for mGluR5, 2-methyl-6-(phenylethynyl)pyridine (MPEP) and 3-[(2-methyl-1,3-thiazol-4-yl)ethynyl]pyridine (MTEP) produce anxiolytic-like effects in a number of preclinical assays of stress and anxiety in rodents, which are similar in magnitude to the effects observed using clinically available anxiolytic drugs, including benzodiazepines. However, chronic administration of mGluR5 antagonists produced adverse effects and the development of tolerance to the potentially beneficial effects of these compounds.

Figure 2:
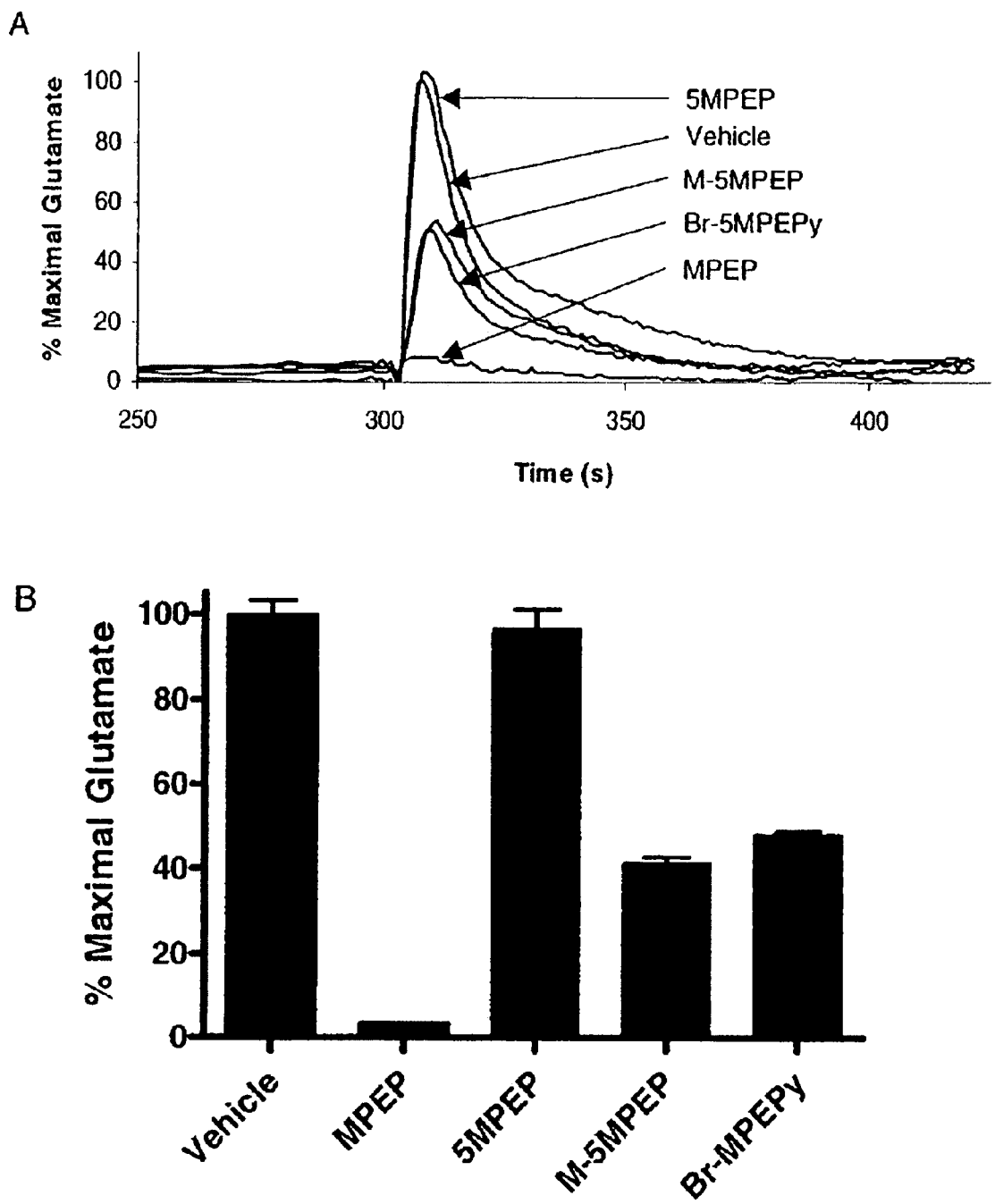
FIG. 2. MPEP analogs do not fully antagonize the mGluR5 receptor response to glutamate in rat cortical astrocytes. (A) Representative traces show mGluR5 response induced by glutamate in the presence of MPEP and MPEP analogs. Compounds (10 μM) were added to cells loaded with a calcium sensitive dye and incubated for 5 min. A nearly maximal concentration of glutamate was added and the calcium response measured by the FDS S plate reader. (B) Bar graph illustrates the means of three independent experiments plotted as a percentage of the maximum response to glutamate. Error bars represent SEM.
Figure 3:
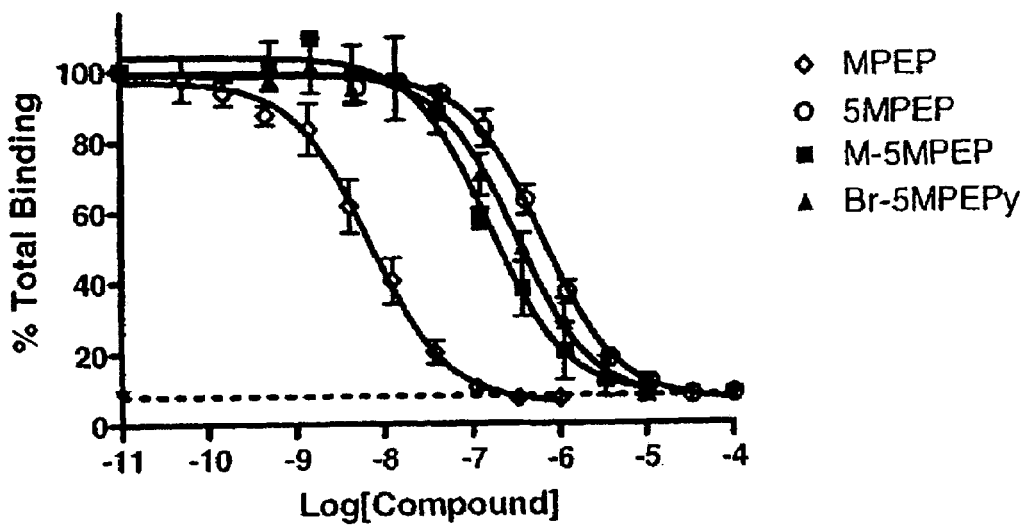
FIG. 3. MPEP analogs inhibit the binding of [3H]methoxyPEPy to membranes from cells expressing mGluR5. Membranes prepared from rat mGluR5 HEK293a cells (10 μg/well) were incubated with radiolabeled MPEP analog [3H]methoxyPEPy (2 nM) in the presence of varying concentrations of MPEP analogs for 60 min at room temperature. Samples were filtered through glass fiber filters and washed extensively. Non-specific binding was estimated with 5 μM MPEP. Concentration response curves were generated from the means of three separate experiments. Error bars represent SEM.

The present invention is predicated on the modulation of mGluR5 through partial antagonism of this receptor. It represents a novel mechanism for producing anxiolytic-like effects and other desirable CNS effects without subsequent dose-limiting side effects including sedation, motor impairment, and the development of tolerance. More particularly, the novel compounds of the invention have been shown to partially antagonize the mGluR5 response to glutamate in rat cortical astrocytes (FIG. 2). In addition, both M-5MPEP and Br-5MPEPy fully inhibited the binding of the MPEP analog [3H]methoxyPEPy to mGluR5 membranes obtained from HEK cells stably expressing the receptor with inhibition constants of 145+60 and 182±50 nM, respectively (FIG. 3).

Figure 4:
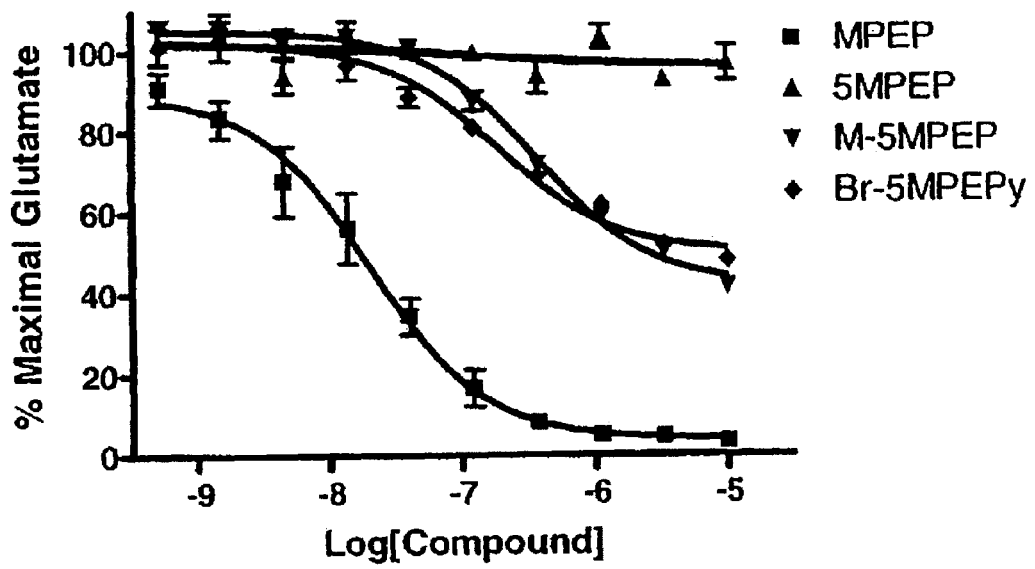
FIG. 4. 5MPEP does not antagonize the mGluR5 receptor response to glutamate in rat cortical astrocytes. Varying concentrations of MPEP and MPEP analogs were added to calcium sensitive dye loaded cells and incubated for 5 min. A nearly maximal concentration of glutamate was added and the calcium response measured by the FDSS plate reader. Concentration response curves were generated from the mean data of three experiments. Data are plotted as a percentage of the maximum response to glutamate. Error bars represent SEM.
Figure 5:
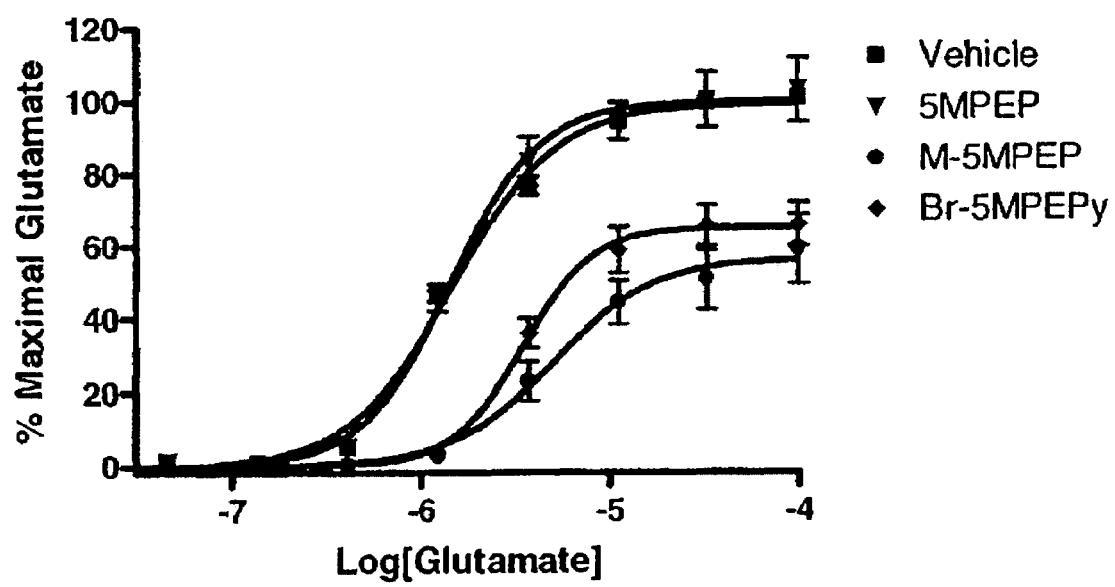
FIG. 5. 5MPEP does not alter the concentration response relationship of mGluR5 to glutamate. MPEP analogs (10 μM) were added to calcium sensitive dye loaded cells and incubated for 5 min. A range of glutamate concentrations was added and the calcium response measured by the FDSS plate reader. Concentration response curves were generated from the mean data of at least three experiments. Data are plotted as a percentage of the maximum response to 100 M glutamate. Error bars represent SEM.
Figure 6:
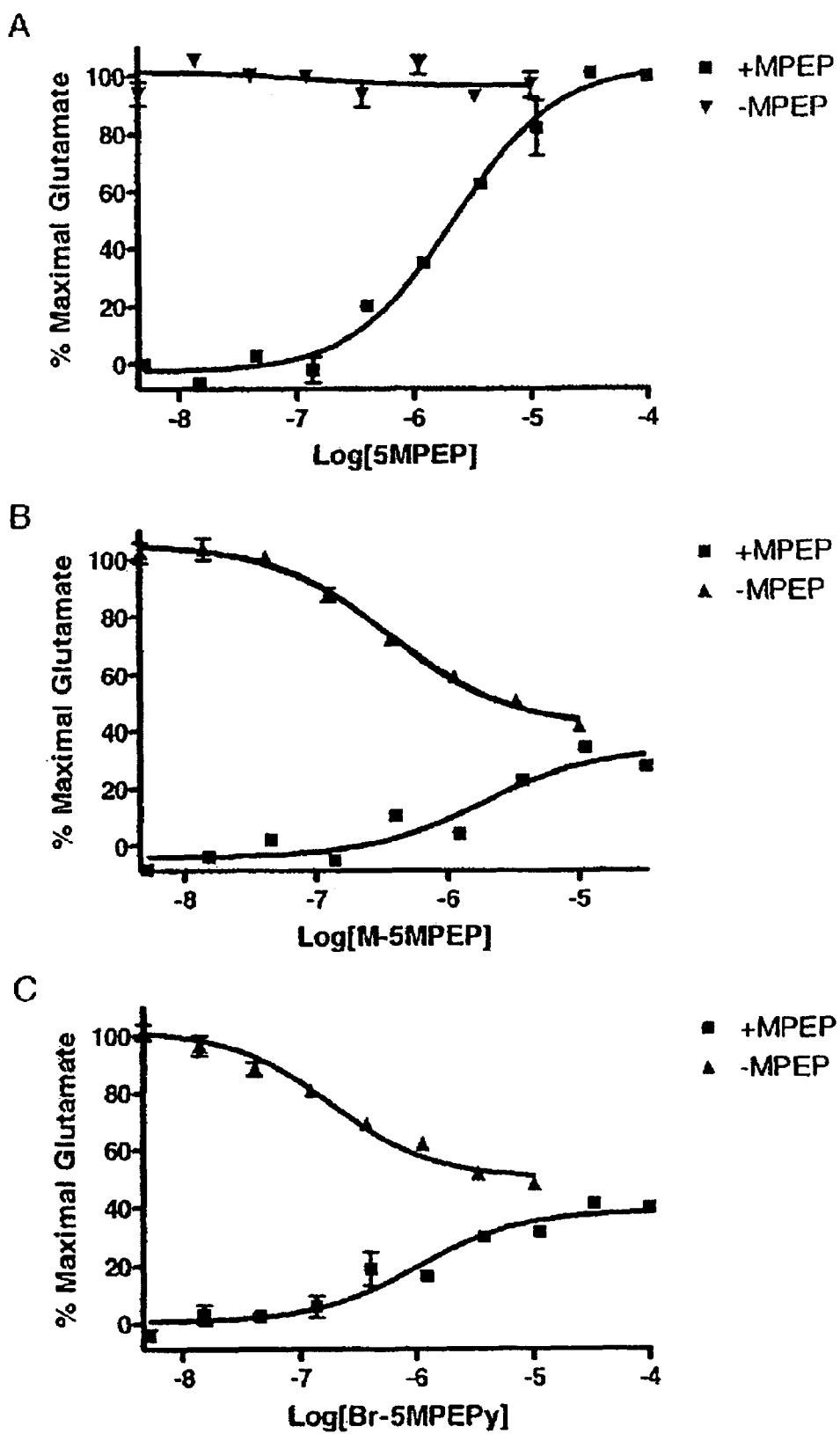
FIG. 6. 5MPEP reduces allosteric inhibition of mGluR5 by MPEP in a concentration dependent manner. Varying concentrations of (A) 5MPEP, (B) M-5MPEP and (C) Br-5MPEPy were added to calcium sensitive dye loaded cells followed 1 min later by addition of a single concentration of MPEP (50 nM). After a 5 min incubation, a nearly maximal concentration of glutamate was added and the calcium response measured by the FDSS plate reader. For comparison, the concentration response relationship of each compound on the response to glutamate alone is shown. Concentration response curves were generated from the mean data of three experiments. Data are plotted as a percentage of the maximum response to glutamate. Error bars represent SEM.

To further characterize the partial antagonist properties of M-5MPEP and Br-5MPEPy, both compounds were tested for antagonism of mGluR5-mediated increases in intracellular calcium across a wide range of concentrations. The concentration response curves of M-5MPEP and Br-5MPEPy were both shifted to the right approximately 10-fold when compared to MPEP, while the maximal inhibition of both compounds was approximately 50% that of MPEP (FIG. 4). Moreover, M-5MPEP and Br-5MPEPy blocked the mGluR5 response to glutamate and induced a rightward and partial downward shift of the glutamate concentration response curve, indicating they behave as partial non-competitive antagonists (FIG. 5). In FIG. 6, the inhibitory activity of MPEP on the glutamate response was only partially blocked by both M-5MPEP and Br-5MPEPy. Taken together the observed partial non-competitive antagonist effects of M-5MPEP and Br-5MPEPy result in subsequent anxiolytic-like effects in preclinical models of stress and anxiety in rodents, similar in magnitude to previously reported anxiolytic-like effects observed using benzodiazepines and MPEP but without the development of tolerance or dose-limiting side effects. In addition, these compounds will have beneficial effects in multiple other disorders of the nervous system where mGluR5 antagonists have been shown to be effective.

In the following Examples, MPEP and DFB were obtained from commercial sources (Tocris). CDPPB and 5MPEP were synthesized as previously described (Lindsley et al and Alagille et al, supra). M-5MPEP and Br-SMPEPy and their precursor were synthesized as follows:

EXAMPLE 1

5-Methyl-2-trimethylsilanylethynyl-pyridine

To a solution of 2-bromo-5-methylpyridine (17.4 mmol) in 50 mL of degassed Et3N was added trimethylsilylacetylene (19.1 mmol), CuI, (1.74 mmol) and trans-dichlorobis(triphenylphosphine)palladium (1.74 mmol). The resulting solution was stirred at RT overnight under N2 atmosphere. The black solution was then hydrolyzed with 30 mL of H2O and extracted with Et2O (3×30 mL). Purification of the residue by column chromatography (hexane/Et2O 9/1) provided the desired compound in 81% yield as brown oil. 1H NMR (CDCl3) δ ppm: 0.08 (s, 9H, CH3); 2.30 (s, 3H, CH3); 7.41 (d, 1H, J=7.5 Hz, CHAT), 7.59 (d, 1H, J=7.5 Hz, CHAr); 8.41 (s, 1H, CHAr). 13C NMR (CDCl3) δ ppm: 0.0 (3C, CH3); 18.9 (1C, CH3); 94.0 (1C, C≡C); 104.7 (1C, C≡C); 126.1 (1C, CHAr); 132 (1C, Cq); 135.2 (1C, CHAr); 141.6 (1C, Cq); 150.7 (1C, CHAr).

EXAMPLE 2

2-(3-Methoxyphenylethynyl)-5-methylpyridine (M-5MPEP)

To a solution of 5-methyl-2-trimethylsilanylethynylpyridine (5.32 mmol) in 25 mL degassed N,N-dimethylformamide was added successively 3-bromoanisole (6.96 mmol), CuI (0.57 mmol), Et3N (21.2 mmol) and trans-dichlorobis(triphenylphosphine)palladium (29 mmol). The resulting mixture was warmed to 70° C., Bu4NF (5.85 mmol) was added drop-wise, and the reaction was stirred at this temperature 2 h. After cooling, 20 mL of H2O was added and the resulting solution was extracted with EtOAc (4×20 mL). The organic layer was washed with saturated NaCl (3×20 mL), dried over Na2SO4 and evaporated to dryness. Purification of the residue by column chromatography provided M-5MPEP in 52% yield as a yellow oil. HCl salts were prepared by adding 2 M HCl/Et2O to a solution of free base in EtOAc and isolated by suction filtration. 1H NMR (CDC13) δ ppm: 2.20 (s, 3H, CH3); 3.67 (s, 3H, CH3); 6.79 (ddd, 1H, J=8.5, 2.5, 1.0 Hz, CHAr); 7.01-7.02 (m, 1H, CHAr); 7.07 (dt, 1H, J=8.5, 1.0 Hz, CHAr); 7.13 (t, 1H, J=8.5 Hz, CHAr); 7.29 (d, 1H, J=7.5 Hz, CHAr); 7.33 (dd, 1H, J=7.5, 2.5 Hz, CHAr); 8.32 (s, 1H, CHAr). 13C NMR (CDCh) δ ppm: 18.8 (1C, CH3); 55.6 (1C, CH3); 88.8 (1C, C≡C); 88.9 (1C, C≡C); 115.9 (1C, CHAr); 116.9 (1C, CHAr); 123.8 (1C, Cq); 124.6 (1C, CHAr); 127.0 (1C, CHAr); 129.6 (1C, CHAr); 133.1 (1C, Cq); 137.0 (1C, CHAr); 140.8 (1C, Cq); 150.9 (1C, CHAr); 159.6 (1C, Cq). HCl salt mp 171-172° C. Anal. C 15H13NO HCl 0.2H20) C, H, N.

EXAMPLE 3

3-(6-Methylpyridin-2-ylethynyl)-5-bromopyridine (Br-5MPEPy)

To a solution of 5-methyl-2-trimethylsilanylethynylpyridine (5.32 mmol) in 25 mL degassed N,N-dimethylformamide was added successively 3,5-dibromopyridine (6.96 mmol), CuI (0.57 mmol), Et3N (21.2 mmol) and trans-dichlorobis(triphenylphosphine) palladium (29 mmol). The resulting mixture was warmed to 70° C., Bu4NF (5.85 mmol) was added drop-wise, and the reaction was stirred at this temperature 2 h. After cooling, 20 mL of H2O was added and the resulting solution was extracted with EtOAc (4×20 mL). The organic layer was washed with saturated NaCl (3×20 mL), dried over Na2SO4 and evaporated to dryness. Purification of the residue by column chromatography provided Br-5MPEPy in 41% yield as a clear oil. HCl salt was prepared by adding 2 M HCl/Et2O to a solution of free base in EtOAc and isolated by suction filtration. 1H NMR (CDCh) δ ppm: 2.24 (s, 3H, CH3); 7.32 (d, 1H, J=7.5 Hz, CHAr); 7.38 (dd, 1H, J=7.5, 2.5 Hz, CHAr); 7.86 (t, 1H, J=2.5 Hz, CHAr); 8.34 (s, IH, CHAr); 8.50 (d, 1H, J=2.5 Hz, CHAr); 8.59 (d, IH, J=2.5 Hz, CHAT) 13c NMR (CDCh) δ ppm: 18.9 (1C, CH3); 83.6 (1C, C≡C); 93.3 (1C, C≡C); 120.3 (1C, Cq); 121.4 (1C, Cq); 127.2 (1C, CHAr); 133.9 (1C, Cq); 137.0 (1C, CHAr); 139.6 (1C, Cq); 141.2 (1C, CHAr); 150.4 (1C, CHAT); 150.7 (1C, CHAr); 151.1 (1C, CHAr). HCl salt mp 166-168° C. Anal. (C13H9N2·HCl·0.6H20) C, H, N.

EXAMPLE 4

Rat Cortical Astrocytes

Rat cortical astrocytes were prepared as described by Peavy et al. ((2001) Metabotropic glutamate receptor 5induced phosphorylation of extracellular signal-regulated kinase in astrocytes depends on transactivation of the epidermal growth factor receptor. J Neurosci 21:9619-28). In brief, neocortices from 2-4 day old Sprague Dawley rat pups were dissected and dissociated in DMEM by trituration with 1 ml pipette tips. The cells were then centrifuged and resuspended in DMEM (containing 1 mM sodium pyruvate, 2 mM L-glutamine, Pen-Strep) supplemented with 10% FBS in T75 tissue culture flasks; the medium was changed the next day. Cell cultures were maintained at 37° C. in an atmosphere of 95% air/5% CO2 for 6-8 days. Cells were shaken overnight (280-310 rpm) to remove oligodendrocytes and microglia.

EXAMPLE 5

Calcium Fluorescence Assay

Secondary astrocytes were trypsinzed and replated into poly-D-Lysine coated 384 well plates (Greiner) at 10K cells/well in 20 μL growth medium (DMEM containing 10% FBS, 20 mM HEPES, 2 mM L-glutamine and antibiotic/antimycotic). The second day the medium was changed to growth medium and G-5 supplement (Invitrogen) containing EGF (10 ng/ml), basic fibroblast growth factor (5 ng/ml), insulin (5 μg/ml), and other factors. The cells were nearly confluent within 2 days and resembled the polygonal astrocytic appearance in vivo. The fourth day, approximately 20 hours before experiments, the medium was changed to glutamine free DMEM containing 5% dialyzed FBS, 20 mM HEPES and antibiotic/antimycotic. On day five medium was removed from the plate and the cells incubated with 20 μL of 1 μM Fluo-4AM (Molecular Probes) in assay buffer (Hank's balanced salt solution, 20 mM HEPES and 2.5 mM Probenecid) for 1 h at 37° C. Dye was removed and 20 μL assay buffer was added. Ca2+ flux was measured using the Functional Drug Screening System (FDSS6000 by Hamamatsu).

Compounds were diluted into assay buffer to a 5× stock which was applied to the cells. For neutral measurements, cells were preincubated with the test compounds for 1 min, potentiator or antagonist was added, and the cells incubated for an additional 5 min. Cells were then stimulated for 2 min with an appropriate concentration of glutamate. For potentiator and antagonist measurements, cells were preincubated with the test compounds for 5 min and then stimulated for 2 min with an appropriate concentration of glutamate. Data were collected at ¼ Hz during the preincubation period and at 1 Hz during the glutamate addition phase of the experiment.

Raw data were normalized in a three step process: (1) Cell number and non-uniform illumination/imaging were controlled for based on the initial readings for the well, (2) the signal amplitude for the data point immediately preceding the agonist addition was subtracted from each point on the trace, (3) data were normalized to the maximal response for each experiment. Concentration response curves were generated using Prism 4.0 (GraphPad).

EXAMPLE 6

Radioligand Binding Assays

The allosteric antagonist MPEP analog [3H]methoxyPEPy (Cosford et al., [3H]-methoxymethyl-MTEP and [3H]-methoxy-PEPy: potent and selective radioligands for the metabotropic glutamate subtype 5 (mGluR5) receptor. Bioorg Med Chem Lett 13:351-4, 2003) was used to evaluate the interaction of the test compounds with the allosteric MPEP site on mGluR5. Membranes were prepared from HEK293A cells stably expressing rat mGluR5. Compounds were diluted into assay buffer (50 mM Tris/0.9% NaCl, pH 7.4) to a 5× stock and 20 µL test compound added to each well of a 96 well assay plate. 60 µL aliquots of membranes diluted in assay buffer (10 µg/well) were added to each well. 20 µL [3H]methoxyPEPy (2 nM final concentration in assay buffer) was added and the reaction incubated at room temperature for 60 min with shaking. After the incubation period, the membrane-bound ligand was separated from free ligand by filtration through glass-fiber 96 well filter plates (Unifilter-96, GF/B by Perkin Elmer). The contents of each well was transferred simultaneously to the filter plate and washed 4 times with assay buffer (Brandel Cell Harvester). 30 µL scintillation fluid was added to each well and the membrane-bound radioactivity determined by scintillation counting (TopCount by Perkin-Elmer). Non-specific binding was estimated using 5 µM MPEP.

EXAMPLE 7

Electrophysiology in STN Neurons

Midbrain slices were prepared from 12 to 15 day old Sprague-Dawley rats as previously described (Awad H, Hubert G W, Smith Y, Levey A I and Conn P J (2000). Activation of metabotropic glutamate receptor 5 has direct excitatory effects and potentiates NMDA receptor currents in neurons of the subthalamic nucleus. J Neurosci 20:7871-9 and Marino M J and Conn P J (2002) Direct and indirect modulation of the N-methyl D-aspartate receptor. CUIT Drug Target CNS Neurol Disord 1: 1-16). After decapitation, brains were rapidly removed and submerged in an ice-cold choline replacement solution containing (in mM): choline chloride 126, KCl 2.5, NaH2PO4 1.2, MgCl2 1.3, MgSO4 8, glucose 10, and NaHCO3 26, equilibrated with 95% O2/5% CO2. The brain was glued to the chuck of a vibrating blade microtome (Leica Microsystems, Nussloch GmbH) and 350 µM thick slices were obtained. Slices were transferred to a holding chamber containing normal artificial cerebrospinal fluid (ACSF) (in mM): 124 NaCl, 2.5 KCl, 1.3 MgSO4, 1.0 NaH2PO4, 2 CaCl2, 20 glucose, and 26 NaHCO3, equilibrated with 95% O2/5% CO2 that was maintained at room temperature. In all experiments 5 µM glutathione, 500 µM pyruvate, and 250 µM kynurenic acid were included in the choline chloride buffer and in the holding chamber ACSF to increase slice viability.

Slices were transferred to the stage of a brain slice chamber and continually perfused with ACSF (≈3 ml/min). Neurons in the STN were visualized by the 40× water immersion lens with Hoffman modulation contrast microscope. Patch electrodes were pulled from borosilicate glass on a Narashige vertical patch pipette puller and filled with internal solution (in mM): potassium gluconate 125, NaCl 4, NaH2PO4 6, CaCl2 1, MgSO4 2, BAPTA-tetrapotassium salt 10, HEPES 10, Mg-ATP 2, Na2-GTP 0.3; pH adjusted to 7.3 with 0.5 N KOH. Electrode resistance was 3-7 MS2. All whole cell patch clamp recordings were performed using an Axon MultiClamp 700B amplifier, data were digitized with DigiDatal 322A, filtered (2 kHz) and acquired by the pClamp 9.2 program. After formation of a whole-cell configuration, the recorded neurons were current clamped to −60 mV. Membrane potentials of STN neurons were recorded and the response to mGluR5 receptor activation monitored input resistance was monitored. All compounds were added by addition to the perfusion solution.

A broad range of compounds based on the MPEP scaffold (FIG. 1) were synthesized. Most of the compounds in this series fully inhibit activation of mGluR5 by glutamate. However, it was unexpectedly found that a subtle change in the position of the pyridyl methyl group of MPEP to form 5MPEP (FIG. 1) results in a compound that is completely inactive in inhibiting mGluR5 receptor responses. See Published US Application 2001/0056084. It was surprising that such a close structural analog of MPEP had no inhibitory effect on the mGluR5 response to glutamate. Thus, two related compounds, M-5MPEP and Br-5MPEPy, were synthesized, derived from the potent mGluR5 antagonists M-MPEP and Br-MPEPy containing similar structural changes, to determine whether this lack of effect was unique to 5MPEP or whether changing the position of this methyl group would also impact activity of related compounds. In addition, the previous studies were performed in CHO cells that had been transfected with mGluR5 and it was desired to verify that 5MPEP is inactive as an mGluR5 receptor antagonist in a native system. To accomplish this 5MPEP, M-5MPEP and Br-5MPEPy were tested for their ability to inhibit mGluR5 receptor-mediated calcium transients in cortical astrocytes. Cortical astrocytes were chosen for these studies because they provide a native system that endogenously expresses high levels of mGluR5 but not of other mGlu receptor subtypes (Peavy R D, Sorensen S D and Conn P J (2002) Differential regulation of metabotropic glutamate receptor 5-mediated phosphoinositide hydrolysis and extracellular signal-regulated kinase responses by protein kinase C in cultured astrocytes. J Neurochem 83: 110-8). Consistent with this, the mGlu receptor agonist glutamate induced a robust calcium mobilization response in these cells and this response was fully blocked by 10 µM MPEP (FIG. 2). Consistent with previous studies in a recombinant system, 5MPEP (10 µM) had no inhibitory effect on the mGluR5 response to glutamate. M-5MPEP and Br-5MPEPy partially inhibited glutamate-induced calcium transients in these cells (FIG. 2).

The most obvious explanation for the lack of activity of 5MPEP in inhibiting mGluR5 is that this structural change reduces affinity for the MPEP site on this receptor so that 10 µM does not bind to mGluR5. Likewise, a plausible explanation for the relatively small effect of single concentrations of M-5MPEP and Br-5MPEPy is that the affinities of these compounds are drastically reduced so that 10 µM only partially occupies the MPEP site. However, it is unusual for such a subtle structural change to have such a drastic effect on affinity of a ligand for its site. Thus, the affinities of each of these compounds at the allosteric antagonist site for MPEP were detetinined by measuring their ability to displace binding of a close analog of MPEP, [3H]methoxyPEPy, to membranes prepared from HEK293A cells stably expressing rat mGluR5 (FIG. 3). Interestingly, all three analogs fully inhibited the binding of the MPEP analog to mGluR5 membranes at concentrations in the high nM range. The binding affinities of M-5MPEP and Br-5MPEPy ($K_i$=145±60 and 182±50 nM) were slightly higher than that of 5MPEP ($K_i$=388±48 nM), while all three compounds bound to the receptor binding site with a lower affinity than MPEP ($K_i$=4.72±1.50 nM). MPEP (5 μM) was used to estimate non-specific binding (8% of total binding).

We next determined the effects of a wide range of each of the MPEP analogs on mGluR5 receptor-mediated increases in intracellular calcium (FIG. 4). 5MPEP was inactive as an antagonist of mGluR5 across a range of concentrations that should span the occupancy range for this compound at the MPEP site. Interestingly, M-5MPEP and Br-5MPEPy displayed partial antagonist activity and induced a maximal reduction of the response to glutamate of approximately 50%. The IC50 values of these compounds at inhibiting mGluR5 receptor responses were approximately 300 nM, which is consistent with their affinities at the [3H]methoxyPEPy site. It is an interesting finding from the research on the present invention that 5MPEP does not alter the mGluR5 concentration response relationship to glutamate. MPEP and other full allosteric mGluR5 receptor antagonists induce an insurmountable inhibition of the mGluR5 glutamate concentration response curve and completely inhibit the response to glutamate. Thus, MPEP shifts the glutamate concentration response curve to the right and downward. In contrast, allosteric potentiators of mGluR5 induce a parallel shift of the glutamate concentration response curve to the left. Based on this and the finding that M-5MPEP and Br-5MPEPy are partial antagonists of mGluR5, it was predicted that they would be expected to shift the glutamate concentration response curve to the right and decrease in maximal response. However, they would not be expected to flatten the concentration response relationship of glutamate as is the case for MPEP. Consistent with this prediction, maximally effective concentrations of M-5MPEP and Br-5MPEPy induced a rightward and downward shift of the glutamate concentration response curve, suggesting they behave as partial non-competitive antagonists (FIG. 5).

The finding that 5MPEP does not block the response to a near maximal concentration of glutamate suggests that this compound should not shift the glutamate concentration response curve to the right. However, it is possible that 5MPEP could act as an allosteric potentiator and shift the curve to the left. Interestingly, 5MPEP had no effect on the glutamate concentration response curve, suggesting that it is neither an allosteric antagonist nor potentiator of mGluR5.

It was a further interesting finding that 5MPEP blocks MPEP inhibition of mGluR5 induced calcium mobilization. The finding that 5MPEP binds to the MPEP site but does not alter the glutamate concentration response relationship suggests that this compound must be a neutral or silent ligand at this site. If this is the case, 5MPEP would be expected to competitively block the allosteric antagonist response to MPEP. Based on this hypothesis, it was predicted that 5MPEP would bind to the MPEP site of mGluR5 and compete with MPEP, thereby blocking the inhibitory effects of the allosteric antagonist. In a similar manner, if M-5MPEP and Br-5MPEPy are "partial antagonists" at this site, they should also compete with MPEP for binding and block its effects. However, since M-5MPEP and Br-5MPEPy partially inhibit the response to glutamate, they should only partially block the inhibitory response to MPEP. FIG. 6 shows the effects of multiple concentrations of each of these compounds on the calcium mobilization response to glutamate when added alone and in the presence of MPEP. MPEP (50 nM) induces a robust inhibition of the calcium response of mGluR5 to a nearly maximal concentration of glutamate. The concentration response relationship of modulators 5MPEP, M-5MPEP and Br-5MPEPy for blocking the inhibitory activity of MPEP on the glutamate response was determined. For comparison, the concentration response relationship of each compound on the response to glutamate alone is shown. As predicted, each compound induced a concentration-dependent reduction in MPEP induced inhibition of mGluR5. M-5MPEP and Br-5MPEPy only partially blocked the response to MPEP to the level observed with each compound alone. In contrast, 5MPEP fully blocked the response to MPEP in a concentration-dependent manner with an EC50=2.32±0.21 M. As hypothesized, 5MPEP acts as a neutral allosteric ligand by having no impact on the mGluR5 response alone but being capable of blocking the effects of the antagonist MPEP.

Figure 7:
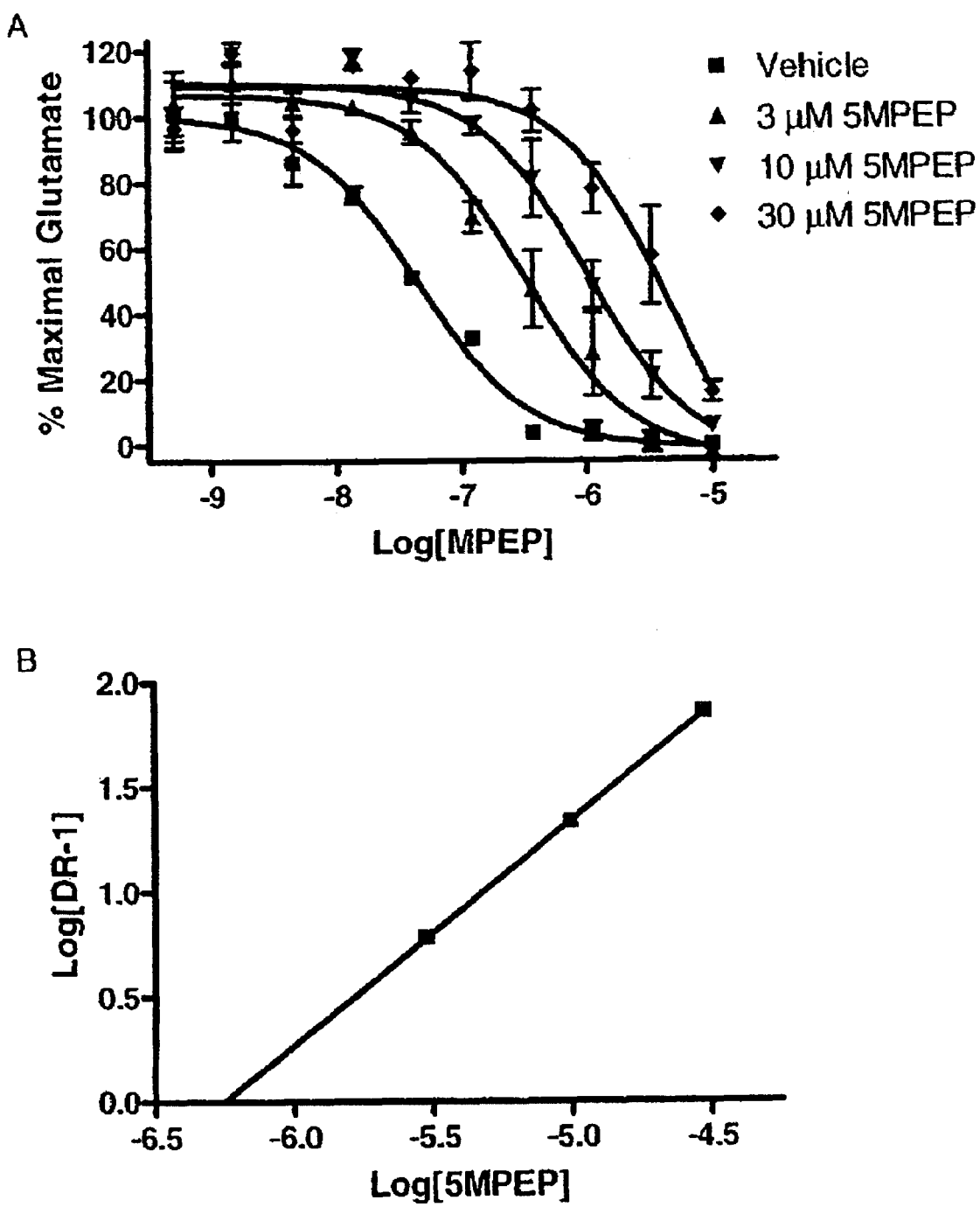
FIG. 7. 5MPEP reduces allosteric inhibition by MPEP in a competitive manner. (A) Multiple concentrations of 5MPEP (3, 10 or 30 μM) were added to calcium sensitive dye loaded cells followed I min later by addition of varying concentrations of MPEP. After a 5 min incubation, a nearly maximal concentration of glutamate was added and the calcium response measured by the FDSS plate reader. Concentration response curves were generated from the mean data of three experiments. Data are plotted as a percentage of the maximum response to glutamate. Error bars represent SEM. (B) Schild analysis of results indicates inhibition of MPEP by 5MPEP is competitive (slope=1.076±0.0094, x-intercept=−6.249).

It was also found that 5MPEP blocks MPEP inhibition of mGluR5 activity in a competitive manner. The binding data indicate that 5MPEP competes with [3H]methoxyPEPy for the MPEP binding site and the functional data demonstrate that 5MPEP blocks the inhibitory effects of MPEP on mGluR5 activity. If 5MPEP blocks MPEP action by competitive interaction with a single allosteric site, 5MPEP should induce a parallel shift in the MPEP concentration response curve to the right. FIG. 7 shows the effects of increasing concentrations of 5MPEP (3, 10 and 30 μM) on the MPEP concentration response relationship. As can be seen, each concentration of 5MPEP induced a parallel rightward shift in the MPEP concentration response curve. Furthermore, a Schild analysis of the effects of 5MPEP on the MPEP concentration response yielded a linear regression with a slope of 1.076±0.01 ($r^2$=0.99) indicating the relationship between 5MPEP and MPEP to be competitive. Extrapolation of the line to the x-intercept established a Ki of 560 nM, a result consistent with the Ki value for 5MPEP at the [3H]methoxyPEPy site as determined by radioligand binding. The Schild regression data combined with radioligand binding data led to the conclusion that 5MPEP binds to the MPEP site and blocks MPEP inhibition of mGluR5 induced calcium mobilization in a competitive manner.

Figure 8:
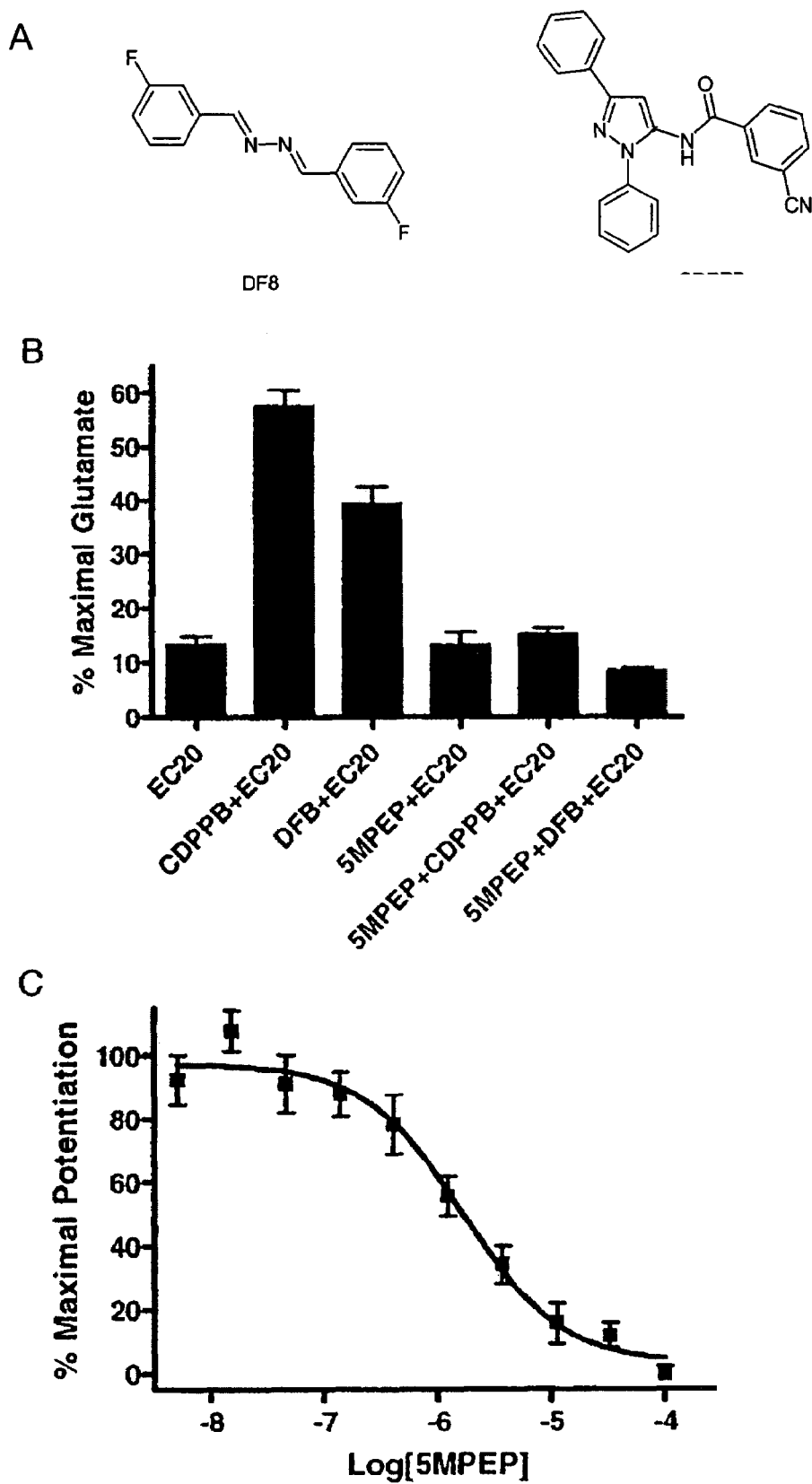
FIG. 8. (A) DFB and CDPPB, two structurally distinct classes of mGluR5 potentiatiors. (B) 5MPEP reduces allosteric potentiation of mGluR5 response by DFB and CDPPB. Either CDPPB (3 μM) or DFB (30 μM) was added to calcium sensitive dye loaded cells and incubated for 5 min. A suboptimal concentration of glutamate was added and the calcium response measured by the FDSS plate reader. For neutral ligand experiments, 5MPEP (30 μM) was added to calcium sensitive dye loaded cells followed 1 min later by addition of a single concentration of CDPPB (3 μM) or DFB (30 μM). After a 5 min incubation, a suboptimal concentration of glutamate was added and the calcium response measured by the FDSS plate reader. The bar graph represents the mean data of three experiments. Data are plotted as a percentage of the maximum response to 100 μM glutamate. (C) 5MPEP reduces allosteric potentiation of mGluR5 response by CDPPB in a concentration dependent manner. Experiments were performed as described in (B). The concentration response curve was generated from the mean data of four experiments. Data are plotted as a percentage of the maximum potentiation of a suboptimal glutamate response. Error bars represent SEM.

Also surprisingly, it was found that 5MPEP blocks potentiation of mGluR5 induced calcium mobilization by multiple structural classes of potentiators. DFB and CDPPB are allosteric potentiators of mGluR5 derived from two different structural scaffolds, both of which are distinct from the MPEP scaffold (FIG. 8A). However, both of these compounds displace [3H]methoxyPEPy binding, leading to the hypothesis that their allosteric potentiator activity is mediated by binding to the same allosteric site as that of MPEP. If this is the case, then the neutral allosteric site ligand 5MPEP should inhibit the allosteric potentiator responses to DFB and CDPPB. Consistent with previous reports in recombinant systems, mGluR5-mediated increases in intracellular calcium in response to a suboptimal concentration of glutamate were potentiated by DFB and CDPPB in rat cortical astrocytes (FIG. 8B). Concentrations of DFB (30 μM) and CDPPB (3 tM) used for this experiment were chosen based on a minimum concentration of each required to elicit a maximal potentiator response. 5MPEP (30 μM) does not alter the mGluR5 response to glutamate alone, but completely blocks the allosteric potentiator responses to both DFB and CDPPB (FIG. 8B). The concentration response relationship of 5MPEP for blocking the potentiator activity of CDPPB was then determined. CDPPB is the more potent potentiator of the two classes, on the glutamate response relationship (FIG. 8C). Inhibition of the potentiator response was found to be concentration-dependent, blocking the response with an IC50=1.71±0.32 M. This is consistent with the concentration response relationship of 5MPEP at blocking the response to MPEP (FIG. 6).

Figure 9:
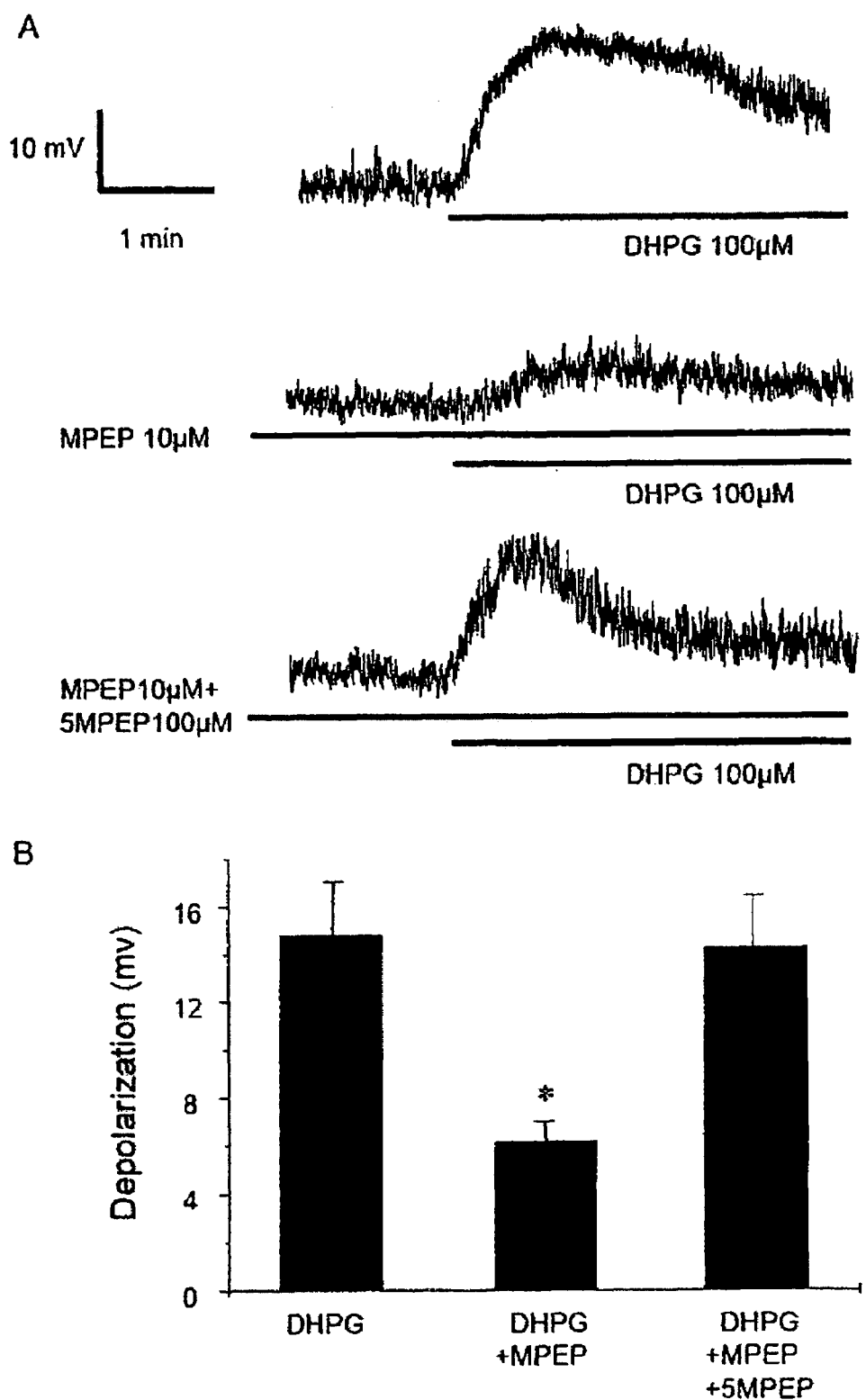
FIG. 9. 5MPEP inhibits the effects of MPEP on mGluR5 receptor responses in STN neurons. (A) Representative traces show depolarization of STN neurons by application of DHPG (100 μM); effect of MPEP (10 μM) on DHPG-induced depolarization; and DHPG-induced depolarization of STN neurons in the presence of MPEP (10 μM) and 5MPEP (100 μM). (B) Bar graph (Mean±SEM) illustrates depolarization of STN neurons by DHPG (n=8 cells), DHPG plus MPEP (n=12 cells), and DHPG in the presence of 5MPEP plus MPEP (n=9 cells). *p<0.01; Student's t test.

It was also found that 5MPEP blocks the effects of CDPPB and MPEP on mGluR5 receptor responses in STN neurons. Discovery of 5MPEP as a neutral ligand with sub-μM affinity at the MPEP site on mGluR5 suggests that this compound could provide a valuable tool for evaluating functional responses to allosteric mGluR5 receptor antagonists and potentiators. Thus, any responses to MPEP or CDPPB that are mediated by actions of these compounds on mGluR5 should be blocked by 5MPEP. It was previously found that MPEP blocks DHPG-induced depolarization of neurons in the subthalamic nucleus (STN) leading to the suggestion that mGluR5 is important for depolarization of these neurons. Thus, the effect of 5MPEP on STN neurons was determined to discover whether this compound has effects in these cells that are consistent with neutral allosteric site activity. Whole-cell recordings were performed from STN neurons in rat midbrain slices in the presence of TTX (500 nM), which block action potential firing. As reported previously, bath application of DHPG (100 μM) induced a robust depolarization in these cells (14.82+2.21 mV; n=8) (FIGS. 9A, 9B). Also, consistent with previous findings, the DHPG-induced response was inhibited by the mGluR5 receptor-selective antagonist MPEP (10 μM) (6.15+0.82 mV; n=12) (FIGS. 9A, 9B), suggesting that it is mediated by activation of the mGluR5. Interestingly, 5MPEP had no effect on membrane potential of STN neurons and did not alter the response to glutamate (FIG. 9A). However, preincubation with 5MPEP (100 pM) for 10 min completely blocked the inhibitory effect of MPEP on DHPG-induced response (14.28±2.1 mV; n=9) (FIGS. 9A, 9B).

Figure 10:
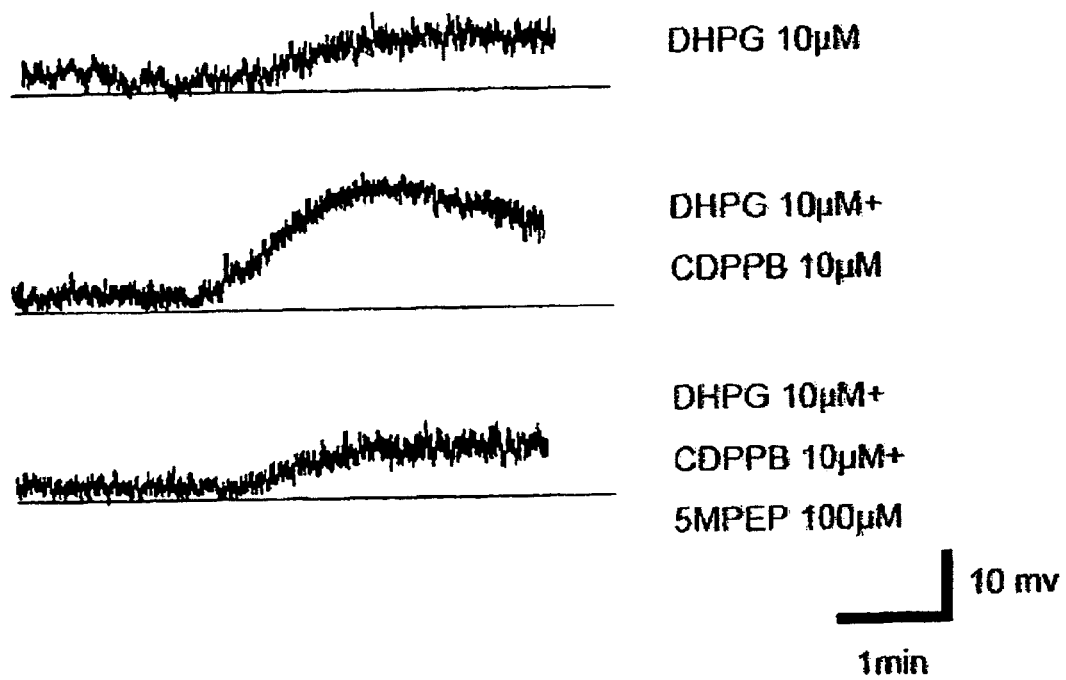
FIG. 10. 5MPEP inhibits the effects of CDPPB on mGluR5 receptor responses in STN neurons. (A) Representative traces show depolarization of STN neurons induced by DHPG (10 μM); potentiation effect of CDPPB (10 μM) on DHPG-induced depolarization; and DHPG-induced depolarization of STN neurons in the presence of CDPPB (10 μM) and 5MPEP (100 μM). (B) Bar graph (Mean±SEM) illustrates depolarization of STN neurons by DHPG (n=6 cells), DHPG plus CDPPB (n=8 cells), and DHPG in the presence of 5MPEP plus CDPPB (n=10 cells).*p<0.01; Student's t test.
Figure 10:
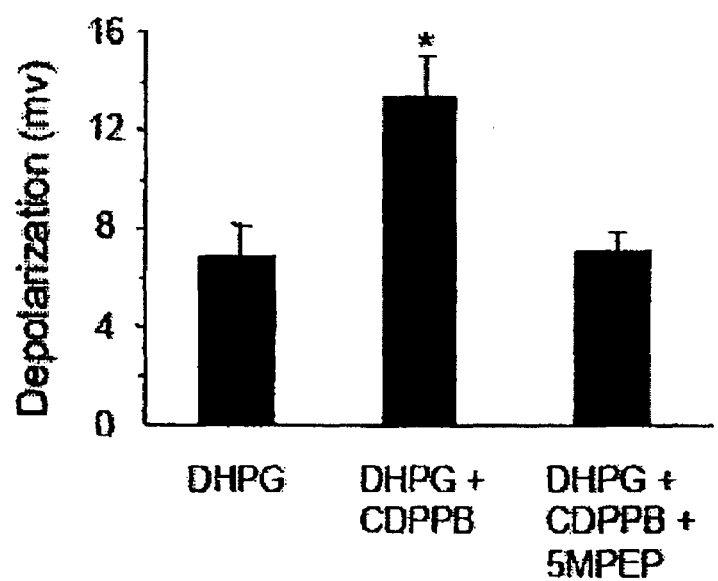
Figure 11:
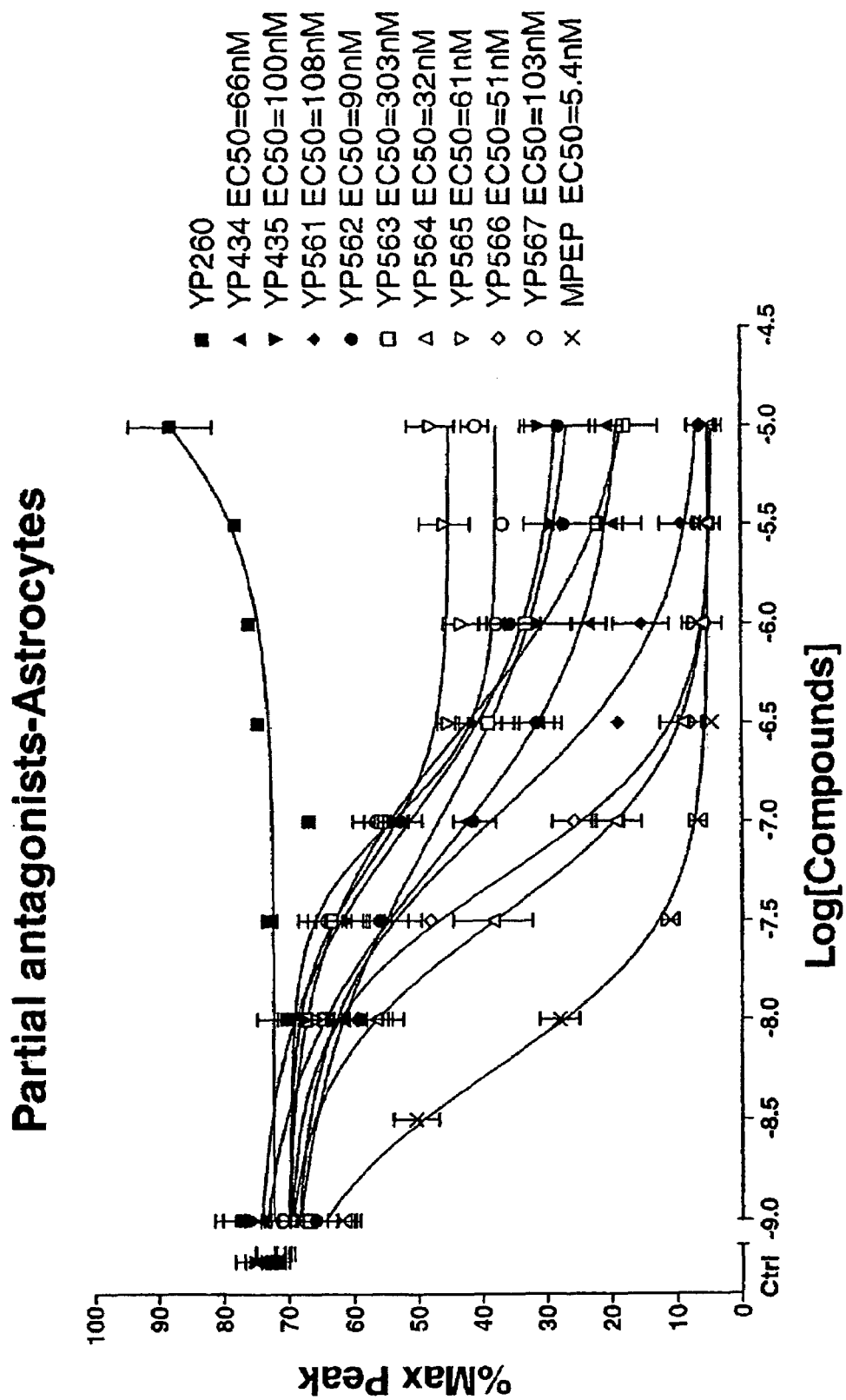
FIG. 11 similarly to the figures above, demonstrates a range of partial activities for several of the compounds depicted below; YP260, YP561, YP562, YP563, YP564, YP565, YP566, YP567.

The effect of the allosteric potentiator CDPPB on the response to a lower concentration of DHPG (10 μM) that induces a submaximal depolarization of STN neurons (6.89+1.22 mV; n=6) was next determined (FIGS. 10A, 10B). Consistent with the allosteric potentiator effects of CDPPB on mGluR5 in recombinant systems and cortical astrocytes, CDPPB (10 μM) induced a robust potentiation of depolarization of STN neurons by DHPG (10 μM) (13.39±1.66 mV; n=8) (FIGS. 10A, 10B). Furthermore, the potentiator response to CDPPB was completely blocked by preincubation with 100 μM 5MPEP (7.05±0.82 mV; n=10). These data provide convincing evidence that CDPPB potentiates electrophysiological responses to mGluR5 receptor activation in STN neurons and indicate that 5MPEP acts as a neutral ligand of mGluR5 in both cortical astrocytes and STN neurons.

5MPEP can be characterized as a novel neutral allosteric site ligand of mGluR5. This compound interacts with the allosteric site on mGluR5 in a manner that is directly analogous to that of a neutral antagonist at an orthosteric neurotransmitter binding site. This is also similar to activity that was recently reported for DCB, an analog of DFB that acts as a neutral ligand at this site. However, unlike 5MPEP, DCB did not have sufficient potency and solubility to allow rigorous characterization or use in more complex systems such as brain slice preparations that are reported for 5MPEP. In addition, M-5MPEP and Br-5MPEPy have been identified as two novel compounds that act as "partial antagonists" at the same allosteric site on mGluR5. While these compounds have some similarities to partial agonists at orthosteric sites, they have actions at a functional level that are fundamentally different from those of partial agonists.

Neutral antagonists at orthosteric sites of GPCRs are similar to 5MPEP in that they bind silently to the orthosteric site and do not activate or decrease constitutive activity of the receptor. However, neutral orthosteric site ligands block the effects of agonists or inverse agonists. Extension of this concept to allosteric sites on GPCRs and the use of this 5MPEP to characterize the pharmacological properties of this allosteric site on mGluR5 provide important insights into the nature of this allosteric site and suggests that ligand interactions with the allosteric site on the mGluR5 receptor follow the same rules of traditional receptor theory that were established with ligand interactions at orthosteric binding sites. Thus, 5MPEP binds to mGluR5 but neither potentiates nor inhibits the response to glutamate when added alone. However, 5MPEP blocks the allosteric antagonist activity of MPEP and the allosteric potentiator activity of CDPPB and DFB. Furthermore, analysis of the effect of 5MPEP on the MPEP concentration response relationship reveals that these ligands regulate functional responses of the receptor in a competitive manner. Thus, analysis of these data using a Schild analysis (Arunlakshana, et al (1959) Some quantitative uses of drug antagonists. Br J Phannacol 14:48-58) suggests a competitive interaction and provides an estimate of the K; value of the neutral ligand that is consistent with that determined by measuring displacement of a radiolabeled ligand to the allosteric site. While analogous to neutral orthosteric ligands, neutral ligands at an allosteric site are fundamentally different in that they are not receptor antagonists. Thus, they do not inhibit the response of mGluR5 to glutamate.

In addition to providing insights into the pharmacological properties of allosteric sites on GPCRs, discovery of 5MPEP provides a valuable tool and expands the toolbox of ligands available for increasing the understanding of the physiological significance of allosteric modulation of GPCRs. While marked progress in the field of allosteric modulation of mGlu receptors and other GPCRs has recently been made, a true understanding of the mechanism by which these ligands regulate receptor function has yet to be established. Also, there exist few tools that allow one to assess the effects of allosteric agonists and antagonists in native systems. Allosteric potentiators and antagonists such as CDPPB and MPEP are playing a central role in developing an understanding of the functional roles of mGluR5 and other GPCRs. By selectively blocking the effects of a potentiator or antagonist while having no effects on the targeted receptor itself, neutral allosteric ligands such as 5MPEP provide exciting new tools that make it possible to evaluate whether a functional response to an allosteric antagonist or potentiator is actually mediated by the targeted receptor. Continued development of neutral ligands will have a major impact on the forward progress of in vivo studies of allosteric modulators of GPCRs and hence, the understanding of their mechanism or action.

In addition to blocking effects of exogenously applied or administered allosteric potentiators or antagonists, 5MPEP provides an exciting tool to aid in studies aimed at deteiniining whether endogenous ligands exist for the allosteric site on mGluR5. While tremendous progress has been made in identifying synthetic compounds that act at allosteric sites on GPCRs, the question as to whether endogenous ligands for these sites remains open. Because 5MPEP is inactive in the absence of an allosteric potentiator or antagonist, it will be of interest to determine whether physiological effects of this compound can be observed under some settings. The present research has found that 5MPEP has no effect on mGluR5 in astrocytes or STN neurons when added alone.

Discovery of the "partial antagonists" of mGluR5 of the present invention also has important implications for the range of activity possible for allosteric site ligands and the potential utility of compounds that interact with the allosteric site. The partial antagonist activity of the compounds of the invention is in some ways analogous to the activity of orthosteric site partial agonists. For both partial antagonists and partial agonists, these compounds will partially block the response of a GPCR to its natural orthosteric ligand. However, unlike partial agonists, M-5MPEP and Br-5MPEPy do not partially activate mGluR5 when added alone. Furthermore, these compounds only partially inhibit the receptor. Such partial antagonists would be useful in settings where there is a need to maintain some level of receptor activity but inhibit effects of excessive receptor activation. This partial antagonist activity is unique to the novel compounds described here and could only be achieved with allosteric site ligands. Thus, this illustrates another important property of ligands at allosteric sites on GPCRs that could not be achieved with orthosteric site ligands and could be useful in discovery of novel therapeutic agents.

A final important point is that previous studies of the action of allosteric potentiators of mGluR5 have been largely restricted to studies in cell lines in which mGluR5 is overexpressed. The present findings in cortical astrocytes and STN neurons suggest that allosteric potentiators of mGluR5 have effects in these native systems that are virtually identical in nature to those previously described in recombinant systems. Furthermore, inhibition of these responses by 5MPEP, which is structurally dissimilar from either DFB or CDPPB, provides strong evidence that these effects of the allosteric potentiators are mediated by mGluR5. These exciting data provide strong support for the potential utility of allosteric potentiators of mGluR5 for increasing activity of this receptor in a range of cells that natively express this receptor.

Thus, it will be apparent to those skilled in the art that the partial mGluR5 antagonists of the invention, of which the above-described specific compounds are only exemplary, are useful for the treatment of any condition or disorder for which the full mGluR5 antagonists are useful.

ABBREVIATIONS USED HEREIN

CNS, central nervous systems; mGlu, metabotropic glutamate receptor; MPEP, 2-methyl-6-(phenylethynyl)-pyridine; methoxy-PEPy, 3-methoxy-5-(2-pyridinylethynyl) pyridine; mGlu, metabotropic glutamate receptor; 5MPEP, 5-methyl-2-phenylethynyl-pyridine; M-5MPEP, 2-(3-methoxyphenyl ethynyl)-5-methylpyridine; Br-5MPEPy, 3-(6-methylpyridin-2-ylethynyl)-5-bromopyridine; CDPPB, 3-cyano-N-(l,3-diphenyl-1 H-pyrazol-5-yl)benzamide; DFB, 3,3'-di fluorobenzaldazine; DCB, 3,3'-dichlorobenzaldazine; DMEM, Dulbecco's modified Eagle's medium; DMSO, dimethyl sulfoxide; FBS, fetal bovine serum; GPCR, G protein-coupled receptor; LBD, ligand binding domain; HEK293A, human embryronic kidney cells; PEI, polyethyleneimine.

REFERENCES

Moghaddam B (2004) Targeting metabotropic glutamate receptors for treatment of the cognitive symptoms of schizophrenia. Psychopharmacology (Berl) 174:39-44.

Peavy R D, Chang M S, Sanders-Bush E and Conn P J Spooren W and Gasparini F (2004) mGluR5 receptor antagonists: a novel class of anxiolytics? Drug News Perspect 17:251-7.

Swanson C J, Bures M, Johnson M P, Linden A M, Monn J A, Schoepp D D. Related Articles, Links Metabotropic glutamate receptors as novel targets for anxiety and stress disorders. Nat Rev Drug Discov. 2005 February;4(2):131-44. Review Spooren W, Gasparini F. Related Articles, Links mGluR5 receptor antagonists: a novel class of anxiolytics? Drug News Perspect. 2004 May;17(4):251-7. Review Kenny P J, Markou A. The ups and downs of addiction: role of metabotropic glutamate receptors. Trends Pharmacol Sci. 2004 May;25(5):265-72. Review.

Marino M J, Conn P I. Related Articles, Links Direct and indirect modulation of the N-methyl D-aspartate receptor. Cun Drug Targets CNS Neurol Disord. 2002 February; 1(1): 1-16. review.

Marino M J, Conn J P. Related Articles, Links Modulation of the basal ganglia by metabotropic glutamate receptors: potential for novel therapeutics. Curr Drug Targets CNS Neurol Disord. 2002 June;1(3):239-50. Review. Erratum in: Curr Drug Target CNS Neurol Disord. 2002 August; 1 (4):449.

Varney M A, Gereau R W 4th. Related Articles, Links Metabotropic glutamate receptor involvement in models of acute and persistent pain: prospects for the development of novel analgesics. Curr Drug Targets CNS Neurol Disord. 2002 June;1(3):283-96. Review.

Moghaddam B. Related Articles, Links Targeting metabotropic glutamate receptors for treatment of the cognitive symptoms of schizophrenia. Psychopharmacology (Berl). 2004 June; 174(1):39-44. Epub 2004 Feb. 19. Review Gasparini F, Kuhn R, Pin J P. Related Articles, Links Allosteric modulators of group I metabotropic glutamate receptors: novel subtype-selective ligands and therapeutic perspectives. Curr Opin Pharmacol. 2002 February;2(1):43-9. Review.

Spooren W P, Gasparini F, Salt T E, Kuhn R. Related Articles, Links Novel allosteric antagonists shed light on mglu(5) receptors and CNS disorders. Trends Pharmacol Sci. 2001 July;22(7):33 1-7 Review.

Alagille D, Baldwin R M, Roth B L, Wroblewski J T, Grajkowska E, Tamagnan G D. Related Articles, Links Functionalization at position 3 of the phenyl ring of the potent mGluR5 noncompetitive antagonists MPEP. Bioorg Med Chem Lett. 2005 Feb. 15;15(4):945-9. PMID: 15686891

Alagille D, Baldwin R M, Roth B L, Wroblewski J T, Grajkowska E, Tamagnan G D. Related Articles, Links Synthesis and receptor assay of aromatic-ethynyl-aromatic derivatives with potent mGluR5 antagonist activity. Bioorg Med Chem. 2005 Jan. 3;13(1):197-209.

Cosford N D, Roppe J, Tehrani L, Schweiger E J, Seiders T J, Chaudary A, Rao S, Varney M A. [3H]-methoxymethyl-MTEP and [3H]-methoxy-PEPy: potent and selective radioligands for the metabotropic glutamate subtype 5 (mGluR5) receptor. Bioorg Med Chem Lett. 2003 Feb. 10;13(3):351-4.

Marino et al., 2001. M. J. Marino, M. Wittmann, S. R. Bradley, G. W. Hubert, Y. Smith and P. J. Conn, Activation of group I metabotropic glutamate receptors produces a direct excitation and disinhibition of GABAergic projection neurons in the substantia nigra pars reticulata. Journal of Neuroscience 21 (2001), pp. 7001-7012.

Awad et al., 2000. H. Awad, G. W. Hubert, Y. Smith, A. I. Levey and P. J. Conn, Activation of metabotropic glutamate receptor 5 has direct excitatory effects and potentiates NMDA receptor currents in neurons of the subthalamic nucleus. Journal of Neuroscience 20 (2000), pp. 7871-7879.

Arunlakshana 0, Schild H O. Some quantitative uses of drug antagonists. 1958. Br J Phalinacol. 1997 February;120(4 Suppl).151-61.

The entire contents and disclosures of each and every reference, including patents, published patent applications and articles are incorporated herein by reference.

What is claimed is:

1. A partial, non-competitive mGluR5 antagonist compound for the treatment of conditions and disorders for which full mGluR5 antagonists are effective.

2. The use compound of claim 1 wherein said compound has the formula:

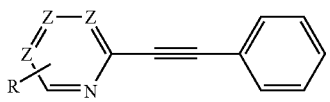

wherein:
Z is, independently N or —CH—, provided that one, and only one Z is N;
R is hydrogen, halogen, alkyl, alkenyl, aryl, or heterocyclic.

3. The compound of claim 2, wherein the compound has one of the formulae:

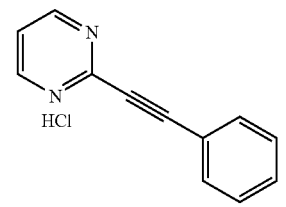

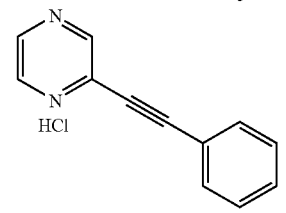

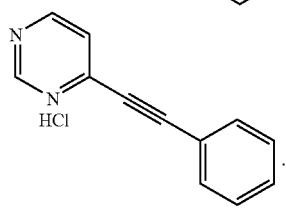

4. A method for the manufacture of a pharmaceutical composition for the treatment of conditions and disorders for which full mGluR5 antagonists are effective comprising combining a partial, non-competitive mGluR5 antagonist compound with a pharmaceutically acceptable carrier.

5. The method of claim 4 wherein said compound has the formula:

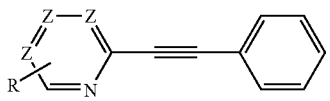

wherein:
Z is, independently N or —CH—, provided that one, and only one Z is N;
R is hydrogen, halogen, alkyl, alkenyl, aryl, or heterocyclic.

6. A method of treating a condition or disorder for which full mGluR5 antagonists are effective, in a subject in need of such treatment, comprising administration to such subject of a therapeutically effective amount of a partial, non-competitive mGluR5 antagonist compound.

7. The method of claim 6 wherein said compound has the formula:

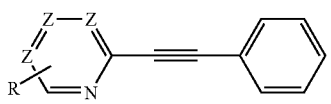

wherein:
Z is, independently N or —CH—, provided that one, and only one Z is N;
R is hydrogen, halogen, alkyl, alkenyl, aryl, or heterocyclic.

8. The method of claim 6, wherein the compound has one of the formulae:

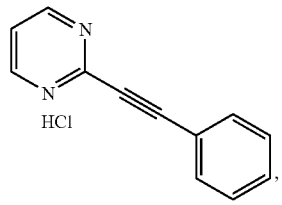

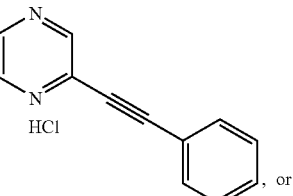

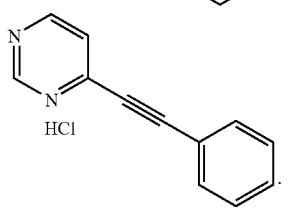

9. The method of claim 6, wherein the compound has the formula:

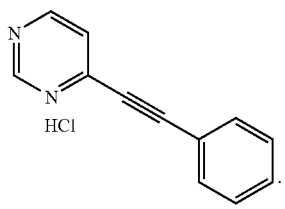

10. The method of claim 6, wherein the condition or disorder is anxiety, epilepsy, schizophrenia, other psychotic disorder, Parkinson's disease, or addictive disorder.

11. The method of claim 6, wherein the condition or disorder is anxiety.

12. The compound of claim 1, wherein the compound has the formula:

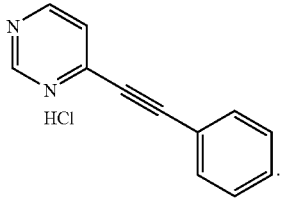

13. The compound of claim 1, wherein the condition or disorder is anxiety, epilepsy, schizophrenia, other psychotic disorder, Parkinson's disease, or addictive disorder.

14. The compound of claim 1, wherein the condition or disorder is anxiety.

15. The method of claim 4, wherein the compound has the formula:

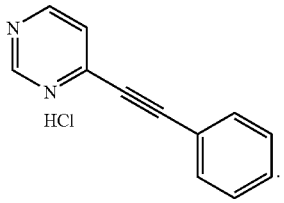

16. The compound of claim 4, wherein the condition or disorder is anxiety, epilepsy, schizophrenia, other psychotic disorder, Parkinson's disease, or addictive disorder.

17. The compound of claim 4, wherein the condition or disorder is anxiety.

18. A pharmaceutical composition for the treatment of conditions and disorders for which full mGluR5 antagonists are effective comprising a partial, non-competitive mGluR5 antagonist compound and a pharmaceutically acceptable carrier.

19. The composition of claim 18, wherein the compound has one of the formulae:

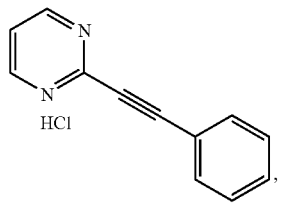

,

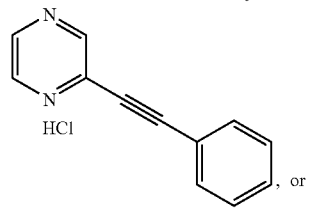

, or

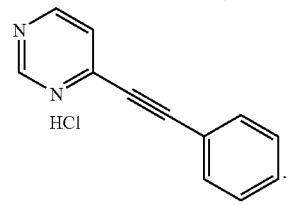

.

20. The composition of claim 18, wherein the compound has the formula:

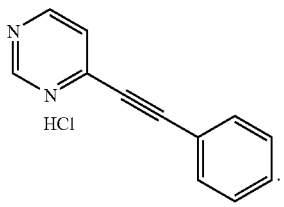

.

21. The composition of claim 18, wherein the condition or disorder is anxiety, epilepsy, schizophrenia, other psychotic disorder, Parkinson's disease, or addictive disorder.

22. The composition of claim 18, wherein the condition or disorder is anxiety.

* * * * *